(12) United States Patent  
Hirose

(10) Patent No.: US 7,991,110 B2  
(45) Date of Patent: Aug. 2, 2011

(54) WEIGHT INSPECTION APPARATUS AND WEIGHT INSPECTION SYSTEM PROVIDED THEREWITH

(75) Inventor: Osamu Hirose, Shiga (JP)

(73) Assignee: Ishida Co., Ltd., Kyoto (JP)

( * ) Notice: Subject to any disclaimer, the term of this patent is extended or adjusted under 35 U.S.C. 154(b) by 75 days.

(21) Appl. No.: 12/519,340

(22) PCT Filed: Feb. 6, 2008

(86) PCT No.: PCT/JP2008/051949  
§ 371 (c)(1),  
(2), (4) Date: Jun. 15, 2009

(87) PCT Pub. No.: WO2008/096787  
PCT Pub. Date: Aug. 14, 2008

(65) Prior Publication Data  
US 2010/0046703 A1    Feb. 25, 2010

(30) Foreign Application Priority Data  
Feb. 8, 2007    (JP) .................................. 2007-029777

(51) Int. Cl.  
*G01B 15/02*    (2006.01)
(52) U.S. Cl. .................. 378/54; 378/51; 378/57
(58) Field of Classification Search .................. 378/51, 378/54, 57  
See application file for complete search history.

(56) References Cited

U.S. PATENT DOCUMENTS

| 6,373,001 B1 | 4/2002 | Kono et al. |
| 6,385,284 B1 | 5/2002 | Parmee |
| 2008/0047760 A1* | 2/2008 | Georgitsis .................. 177/1 |
| 2009/0147987 A1 | 6/2009 | Hirose |

FOREIGN PATENT DOCUMENTS

| JP | 2000-193513 A | 7/2000 |
| JP | 2002-520593 A | 7/2002 |
| JP | 2002-296022 A | 10/2002 |
| WO | WO-2005/111554 A2 | 11/2005 |
| WO | WO-2007/058212 A1 | 5/2007 |

OTHER PUBLICATIONS

Extended European Search Report dated Oct. 29, 2010 for the counterpart European Patent Application No. 08704508.4.

* cited by examiner

*Primary Examiner* — Courtney Thomas  
(74) *Attorney, Agent, or Firm* — Global IP Counselors, LLP

(57) ABSTRACT

A weight inspection apparatus includes a weight obtaining unit, an irradiation unit, a detection unit and an estimated weight calculation unit. The weight obtaining unit is configured to obtain an actual weight of an inspection target object. The irradiation unit is configured to irradiate the inspection target object with energy waves. The detection unit is configured to detect the energy waves irradiated at the inspection target object. The estimated weight calculation unit is configured to calculate an estimated weight of the inspection target object based on a result of detection by the detection unit. The deviation amount calculation unit is configured to calculate a difference between the actual weight obtained by the weight obtaining unit and the estimated weight obtained by the estimated weight calculation unit.

19 Claims, 12 Drawing Sheets

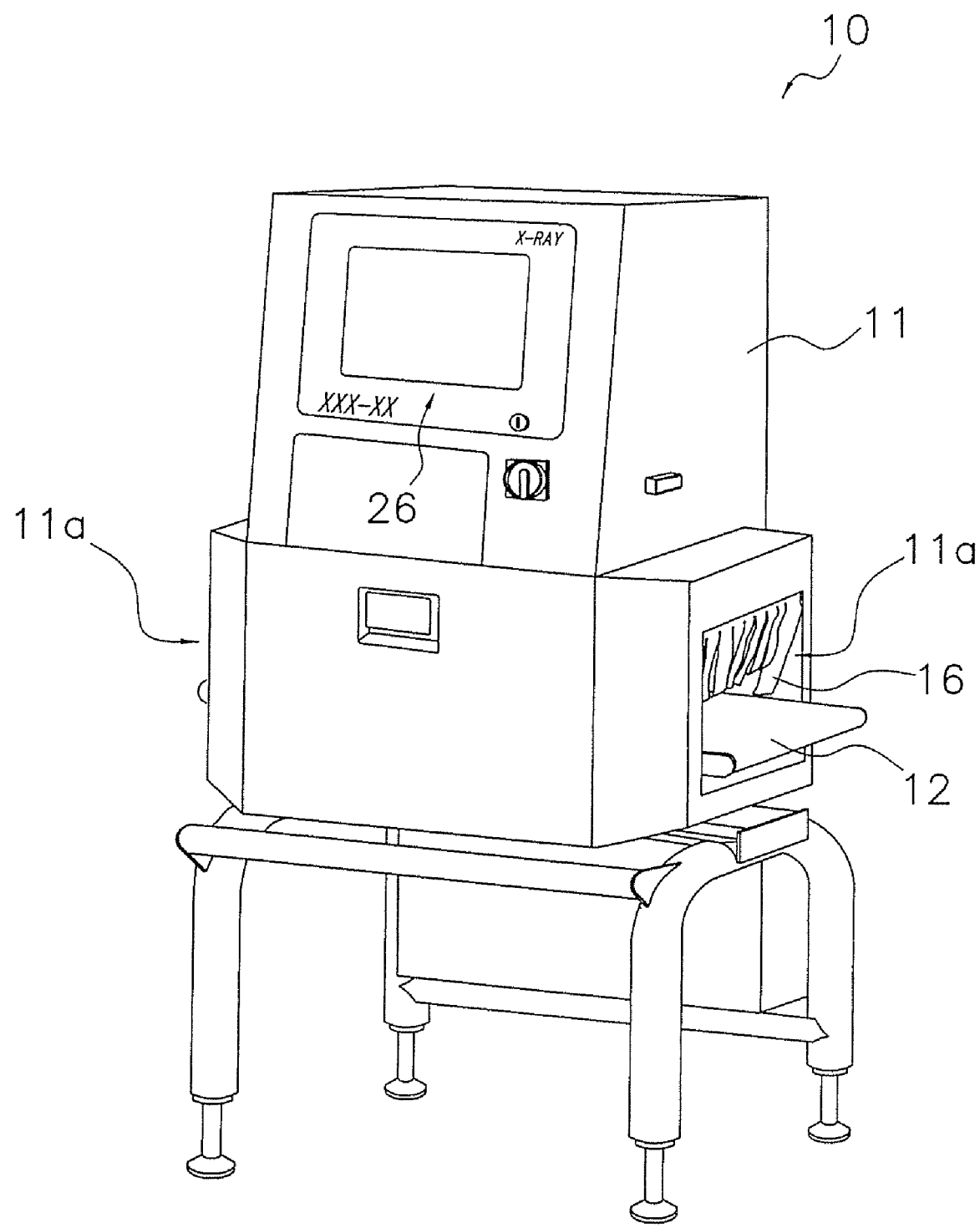
F I G. 2

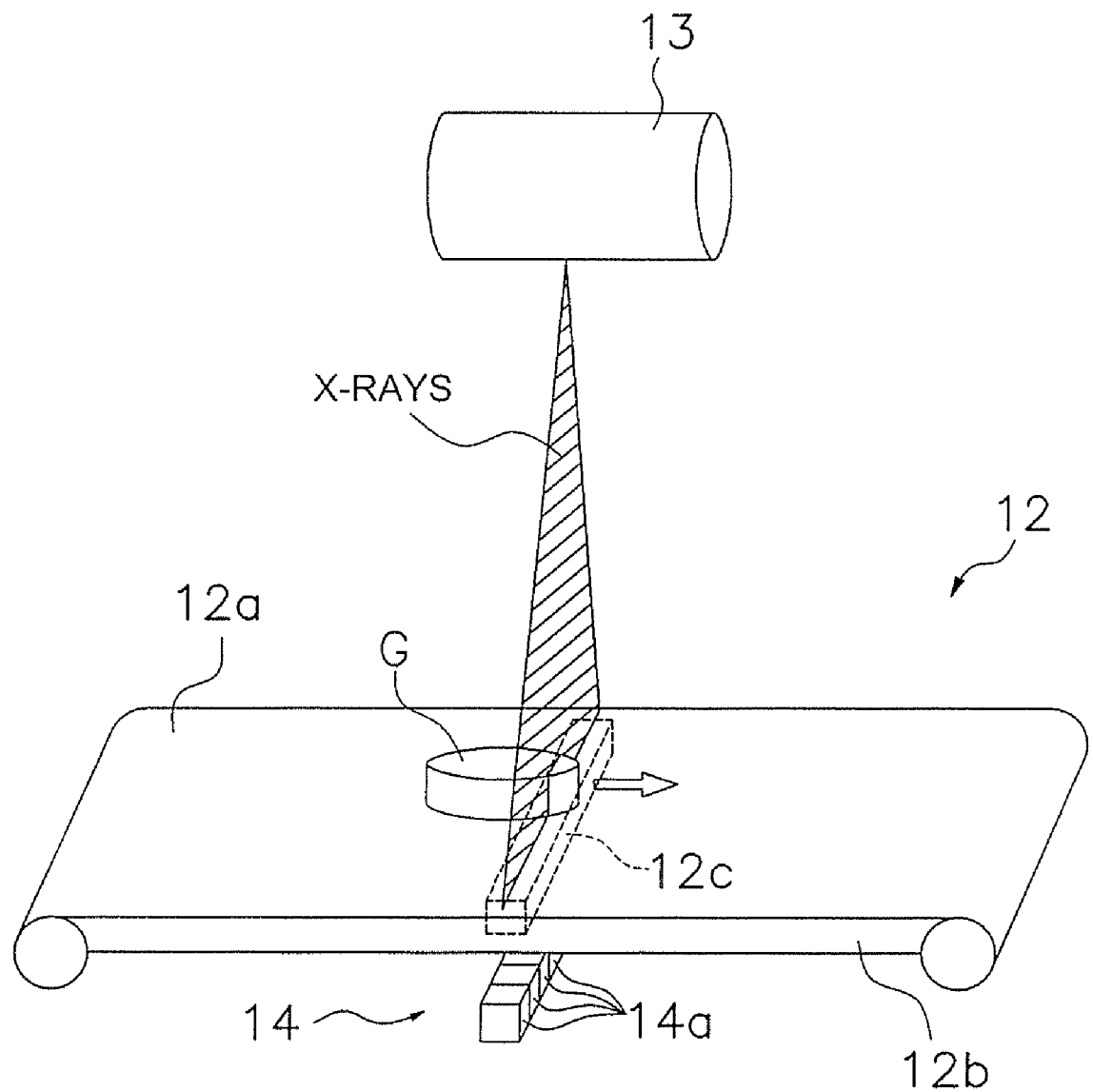
F I G. 3

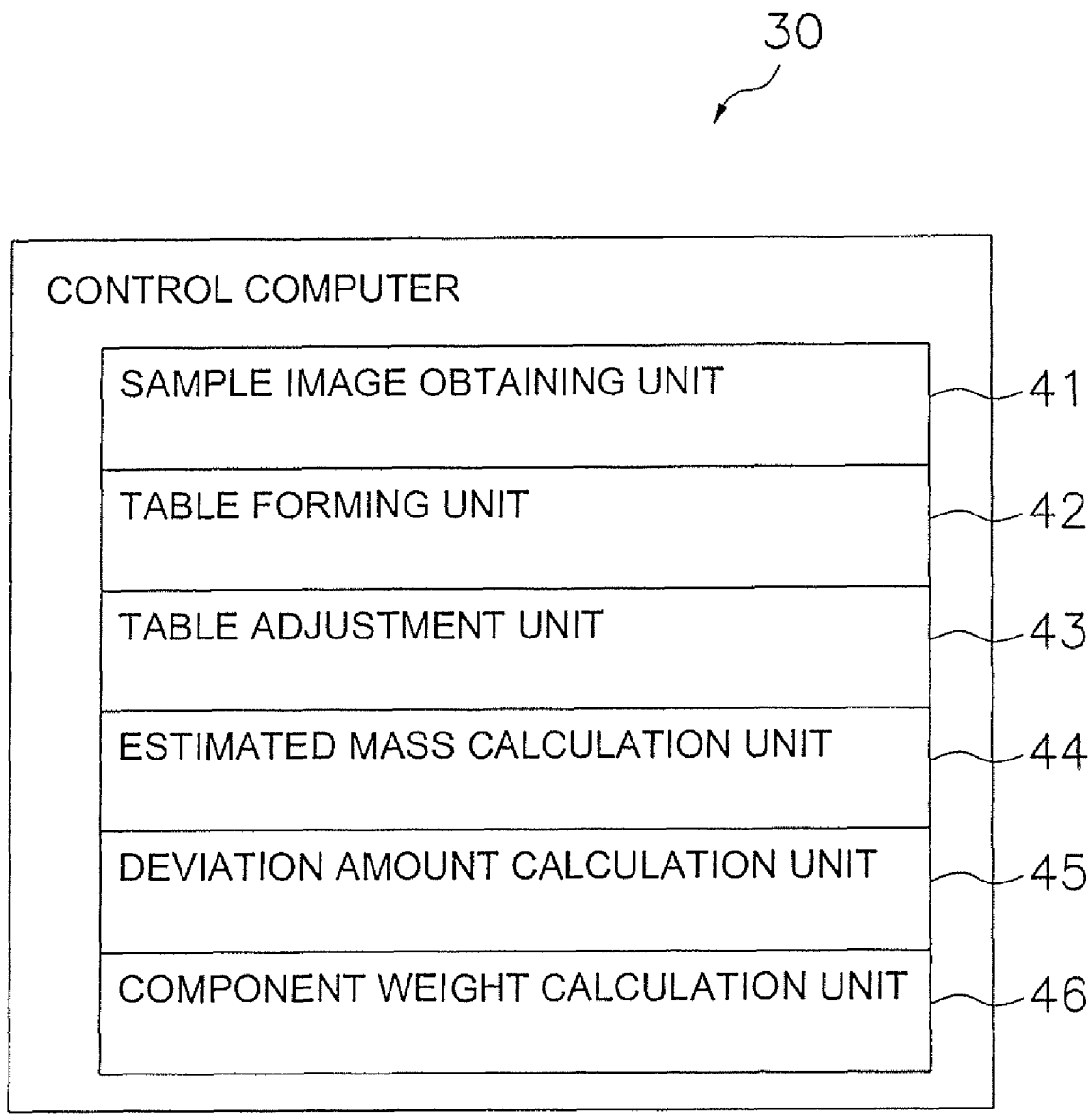
F I G. 6

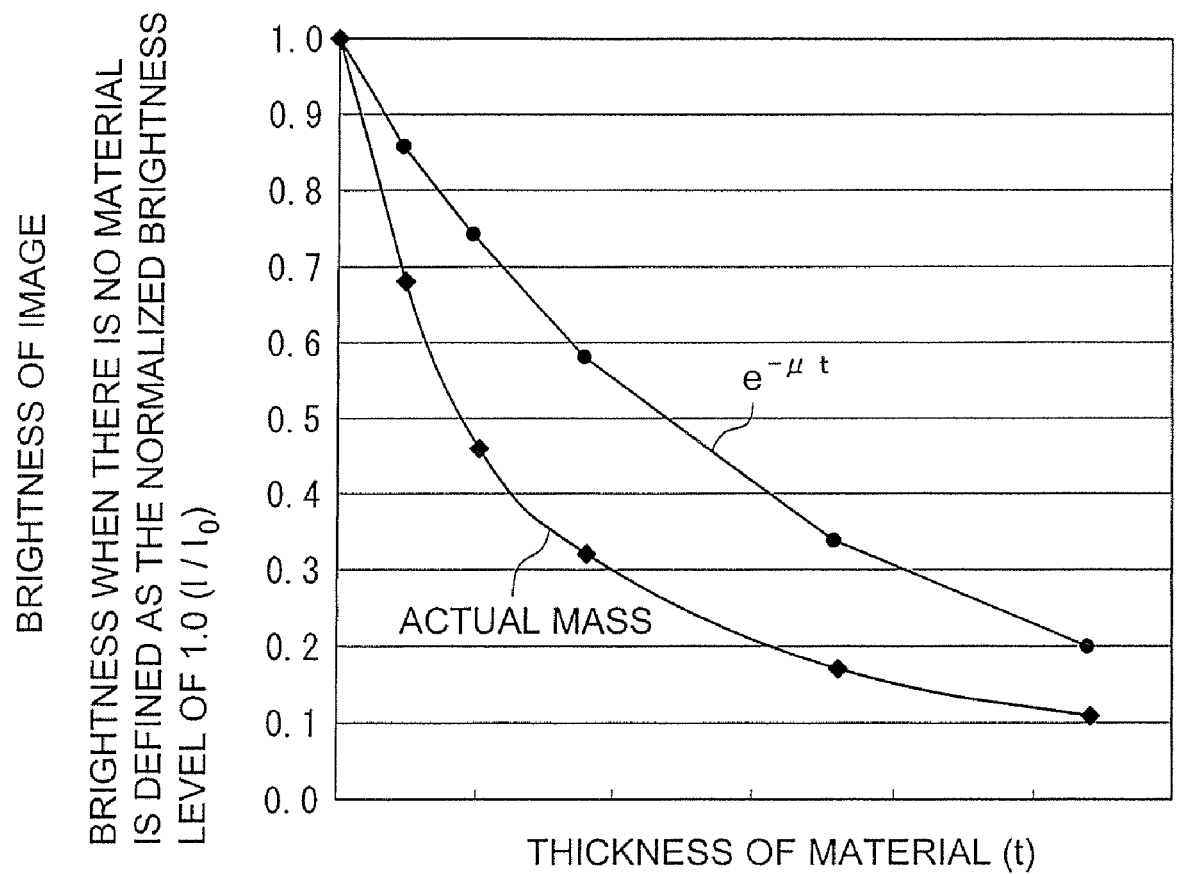
F I G. 7

(a)

(b)

(a)

(b)

(c)

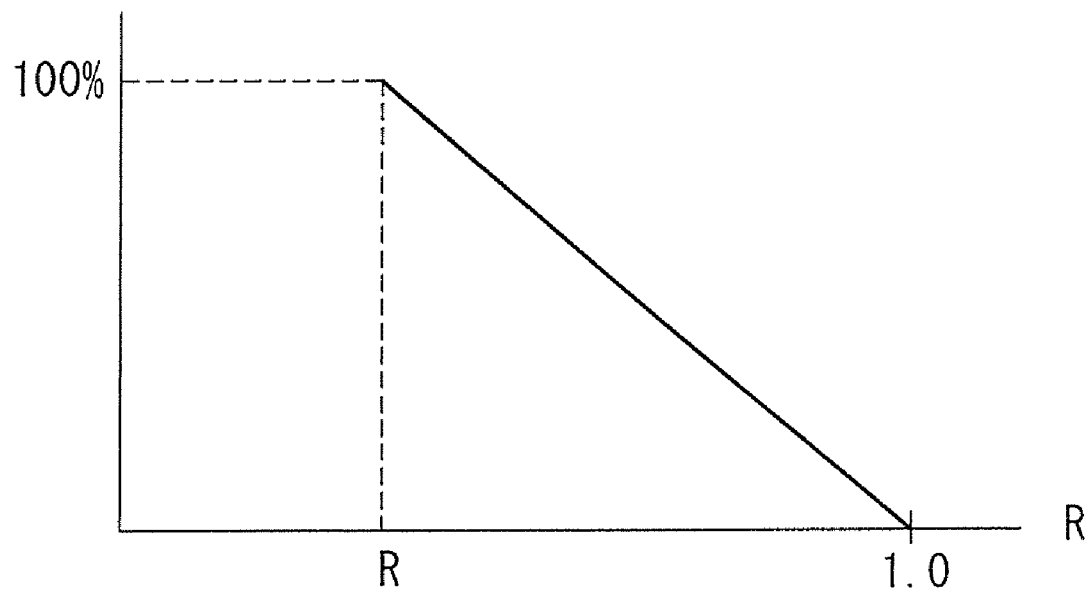
F I G. 11

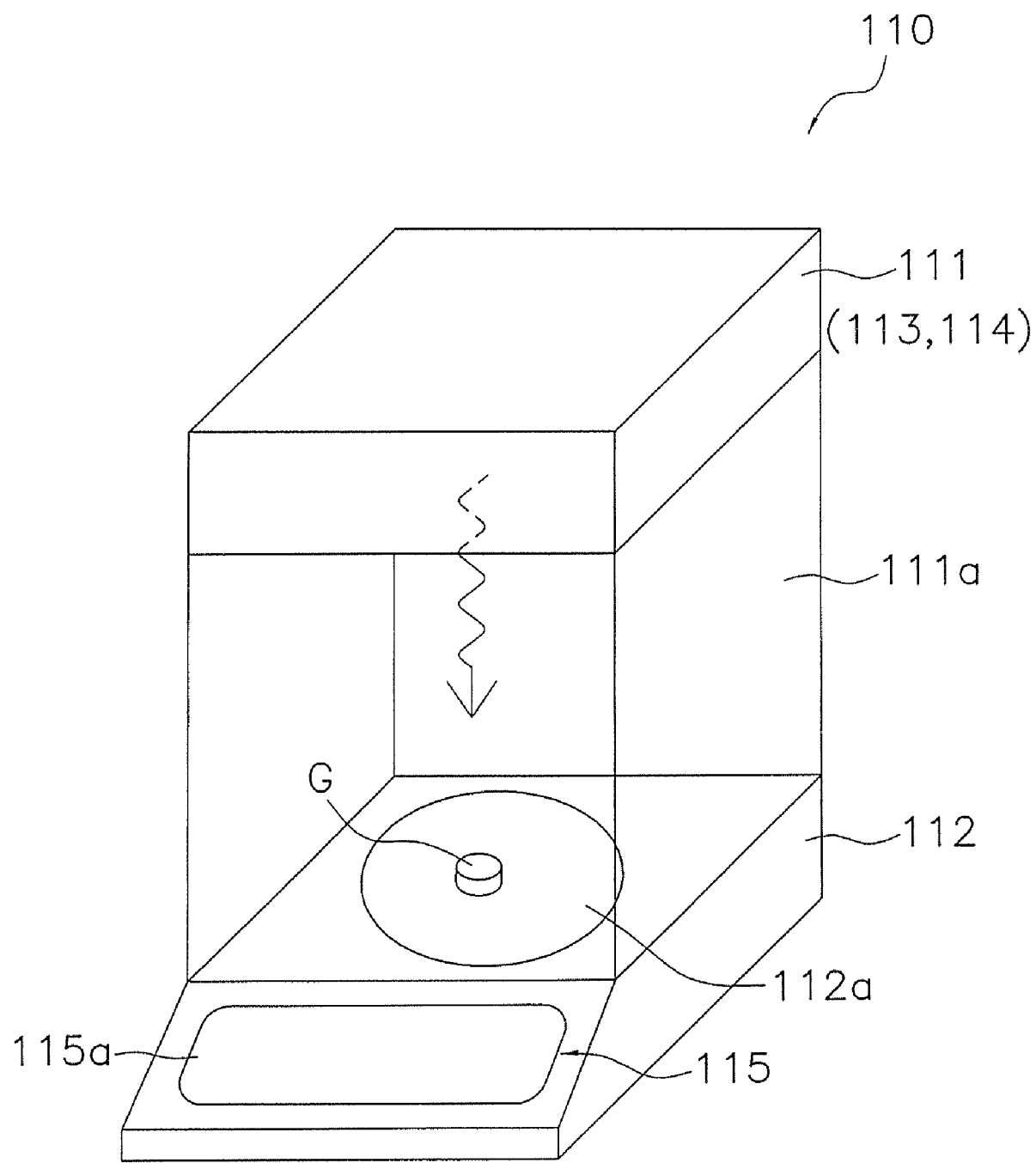
F I G. 12

WEIGHT INSPECTION APPARATUS AND WEIGHT INSPECTION SYSTEM PROVIDED THEREWITH

CROSS-REFERENCE TO RELATED APPLICATIONS

This national phase application claims priority to Japanese Patent Application No. 2007-029777 filed on Feb. 8, 2007. The entire disclosure of Japanese Patent Application No. 2007-029777 is hereby incorporated herein by reference.

TECHNICAL FIELD

The present invention relates to a weight inspection apparatus that estimates the mass of a material based on the amount of transmitted and reflected X-rays and the like used to irradiate the material, and a weight inspection system provided therewith.

BACKGROUND ART

In recent years, an X-ray mass estimation apparatus is used in which a measurement target object is irradiated with X-rays and the mass of the measurement target object is estimated (calculated) based on the amount of transmitted X-rays.

With this X-ray mass estimation apparatus, an X-ray transmission image of the measurement target object is obtained, and then, by utilizing a characteristic that the image appears darker when the thickness of a material in the X-ray transmission image is larger, the mass of the measurement target object is estimated according to the brightness per unit area included in the X-ray transmission image, for example, when the brightness is low, the mass is large, and when the brightness is high, the mass is small.

For example, Japanese Laid-Open Patent Application Publication Nos. 2002-520593 (published on Jul. 9, 2002) and 2002-296022 (published on Oct. 9, 2002) disclose an irradiation monitor for material properties and an X-ray mass estimation apparatus, which, in order to calculate the percentage of a fat content in the meat products, detect the amount of transmitted X-rays that are used to irradiate a material and estimate the weight of the fat content and the entire weight.

DISCLOSURE OF THE INVENTION

However, the conventional X-ray inspection apparatuses described above have the following problem.

Specifically, because the X-ray inspection apparatuses disclosed in the above described publications estimate the weight based only on the amount of X-rays that are transmitted through a material, sometimes it is difficult to calculate the accurate weight with high precision.

An object of the present invention is to provide a weight inspection apparatus capable of calculating with high precision the weight of an inspection target object, and a weight inspection system provided therewith.

A weight inspection apparatus according to a first aspect of the present invention is a weight inspection apparatus configured to detect energy waves irradiated at an inspection target object to calculate the estimated weight of the inspection target object. The weight inspection apparatus includes a weight obtaining unit, an irradiation unit, a detection unit, an estimated weight calculation unit, and a deviation amount calculation unit. The weight obtaining unit is configured to obtain the actual weight of the entire inspection target object. The irradiation unit is configured to irradiate the inspection target object with the energy waves. The detection unit is configured to detect the energy waves irradiated at the inspection target object. The estimated weight calculation unit is configured to calculate the estimated weight of the entire inspection target object based on a detection result by the detection unit. The deviation amount calculation unit is configured to calculate a difference between the actual weight and the estimated weight.

Here, the discrepancy in the actual weight or the estimated weight is promptly detected based on the actual weight of the inspection target object (herein after referred to as "actual weight") obtained, for example, from the weight measuring device provided upstream, and the estimated weight calculated by the weight inspection apparatus.

Here, the weight obtaining unit may indirectly obtain the actual weight as a value measured by a weight checker disposed on the upstream in the above described production line and the like, or may directly obtain the actual weight by providing a weighing instrument in the weight inspection apparatus. Further, the estimated weight calculation unit can adopt a conventional approach in which the estimated weight is calculated by using an image or the like which is created by detecting the amount of transmitted and reflected energy waves used to irradiate the inspection target object. In addition, the above described energy waves include infrared rays, ultraviolet rays, visible light, and the like besides X-rays and terahertz waves.

Accordingly, when the deviation amount between the actual weight and the estimated weight is larger than a predetermined value, for example, this situation can be detected as an occurrence of a defect in either the weight measuring device or the weight inspection apparatus, a correction value to calculate the estimated weight by the weight inspection apparatus can be adjusted, and/or this situation can be used for the calculation of the weight of each of a plurality of components having different specific gravities. As a result, it is possible to improve the precision of the calculated weight of the inspection target object.

A weight inspection apparatus according to a second aspect of the present invention is the weight inspection apparatus according to the first aspect of the present invention, wherein the detection unit is configured to detect the amount of energy waves transmitted through the inspection target object.

Here, the amount of transmitted energy waves used to irradiate the inspection target object is detected to calculate the estimated weight.

Accordingly, the calculation of the estimated weight and the like can be easily performed using an X-ray image and the like which is created based on the amount of transmitted energy waves such as X-rays and the like.

A weight inspection apparatus according to a third aspect of the present invention is the weight inspection apparatus according to the first aspect of the present invention, wherein the detection unit is configured to detect the amount of energy waves reflected from the inspection target object.

Here, the amount of reflected energy waves used to irradiate the inspection target object is detected to calculate the estimated weight.

Accordingly, the absorption spectrum is obtained by detecting reflected energy waves such as terahertz waves and the like, and the calculation and the like of the content percentage and the estimated weight of each component can be easily performed by comparing the above described absorption spectrum with spectrum data of each component contained in the inspection target object.

A weight inspection apparatus according to a fourth aspect of the present invention is the weight inspection apparatus according to any one of the first through third aspects of the present invention, wherein the weight obtaining unit is a weighing unit that measures the actual weight of the inspection target object.

Here, the actual weight of the inspection target object is directly obtained by the weighing unit provided in the weight inspection apparatus.

Accordingly, the actual weight of the inspection target object necessary to determine the estimated weight is easily obtained in the weight inspection apparatus.

A weight inspection apparatus according to a fifth aspect of the present invention is the weight inspection apparatus according to any one of the first through fourth aspects of the present invention, further including a component weight calculation unit configured to calculate the weight of each of a plurality of components having different specific gravities which are contained in the inspection target object, based on the difference between the actual weight and the estimated weight.

Here, for example, when the meat product having a meat portion and a fat portion each having a different specific gravity is used as the inspection target object, the weight of the meat portion and the weight of the fat portion are calculated based on the difference between the actual weight of the entire meat product and the estimated weight determined by weight inspection.

Here, besides the above described meat product, a product such as liquid-base soup that comprises a plurality of components having different specific gravities can be used as the inspection target object. The component weight calculation unit can perform the calculation by substituting the actual weight and the estimated weight into a predetermined calculation formula. Note that the calculation of the weight by the component weight calculation unit includes either one or both of the calculation of the weight and the calculation of the content percentage of each component.

Accordingly, it is possible to improve the precision of the calculated weight because the weight of each component is obtained using both of the actual weight and the estimated weight, compared with a conventional weight inspection apparatus in which the weight of each of the components having different specific gravities is determined based only on the amount of X-rays transmitted through the inspection target object which is detected by each of the two detection units with different inspection sensitivity. In addition, the cost of the weight inspection apparatus can be reduced because there is no need to provide a plurality of detection units such as a line sensor and the like to determine the weights of a plurality of components.

A weight inspection apparatus according to a sixth aspect of the present invention is the weight inspection apparatus according to any one of the first through fourth aspects of the present invention, further including an estimated weight adjusting unit configured to adjust a result of the calculation of the estimated weight by the estimated weight calculation unit, based on the difference between the actual weight and the estimated weight.

Here, for example, when the difference between the actual weight of the inspection target object and the estimated weight obtained by weight inspection is equal to or greater than a predetermined value, it is determined that there is a defect in the calculation of the estimated weight by the weight inspection apparatus, and the estimated weight is adjusted. In other words, the estimated weight is adjusted by checking the precision of the estimation of the weight by the weight inspection apparatus, based on the magnitude of the difference between the actual weight and the estimated weight.

Accordingly, it is possible to easily check whether or not the estimation of the weight by the weight inspection apparatus is performed with high precision. Additionally, when the difference between the actual weight and the estimated weight becomes equal to or greater than a predetermined value, it is possible to prevent a reduction in the precision of the calculation of the estimated weight by, for example, adjusting a correction value which is used when calculating the estimated weight. As a result, it is possible to perform estimation of the weight always with stable precision by calculating the estimated weight with reference to the actual weight.

A weight inspection apparatus according to a seventh aspect of the present invention is the weight inspection apparatus according to any one of the first through sixth aspects of the present invention, wherein the weight obtaining unit is configured to obtain the weight of the inspection target object from the weight measuring device arranged on an upstream side of the weight inspection apparatus.

Here, for example, the weight measuring device which, together with the weight inspection apparatus, constitutes the production line is provided on the upstream side of the weight inspection apparatus, and the weight of each above described component is calculated by obtaining a measured value of the weight of the inspection target object from the weight measuring device.

Accordingly, by arranging the weight inspection apparatus on the downstream side of the weight measuring device included in the production line and the like, it is possible to smoothly perform inspection of the actual weight of the inspection target object, the weight (content percentage) of each component, and the like while the inspection target object is being conveyed to the downstream side in the production line and the like.

A weight inspection apparatus according to an eighth aspect of the present invention is the weight inspection apparatus according to the sixth aspect of the present invention, wherein the component weight calculation unit is configured to calculate the content percentage of a prescribed components among the components contained in the inspection target object based on a following relational expression (1).

$$r = (1 - W2/W1) \times 100/(1-R) \quad (1)$$

(where, r represents the content percentage of the prescribed component A, R represents a weight ratio between when the content percentage of the prescribed component A is 100% and when the content percentage of the prescribed component A is 0%, W1 represents the actual weight of the inspection target object, and W2 represents the estimated weight of the inspection target object).

Here, the component weight calculation unit calculates the content percentage of a specific component using the above described calculation formula (1).

Here, R is calculated in advance based on the weight of the inspection target object when the content percentage of a specific content contained in the inspection target object is 100%.

Accordingly, it is possible to easily determine the weight of each component simply by substituting the actual weight obtained by the weight checker and the like and the estimated weight obtained by the weight inspection apparatus into the above described relational expression (1).

A weight inspection apparatus according to a ninth aspect of the present invention is the weight inspection apparatus according to any one of the first through eighth aspects of the present invention, wherein the estimated weight calculation unit is configured to calculate the estimated weight of the inspection target object using an image created based on the amount of transmitted energy waves detected by the detection unit.

Here, as a method for calculating the estimated weight of the inspection target object, the estimated weight of the inspection target object is determined using data such as shading and the like of an image created based on a result detected by the detection unit of the line sensor and the like.

Accordingly, because the estimated weight can be calculated using an image created by a conventional weight inspection apparatus, the weight of each component can also be smoothly calculated.

A weight inspection apparatus according to a tenth aspect of the present invention is the weight inspection apparatus according to any one of the first through ninth aspects of the present invention, wherein the irradiation unit is configured to irradiate X-rays as the energy waves.

Here, X-rays are used as the energy waves used to irradiate the inspection target object.

Accordingly, it is possible to calculate the weight of a plurality of components contained in the inspection target object and to check the presence of a specific component without reducing the value of the product.

A weight inspection apparatus according to an eleventh aspect of the present invention is the weight inspection apparatus according to any one of the first through ninth aspects of the present invention, wherein the irradiation unit is configured to irradiate terahertz waves as the energy waves.

Here, terahertz waves are used as the energy waves used to irradiate the inspection target object.

Here, terahertz waves are electromagnetic waves having frequency between 0.3 THz and 10.0 THz.

Accordingly, the absorption spectrum is obtained by detecting reflected waves from the inspection target object, and the content percentage, weight, and the like of each component can be determined by comparing the above described absorption spectrum with spectrum data of each component contained in the inspection target object.

As a result, it is possible to calculate the content percentage and the weight of a plurality of components contained in the inspection target object and to check the presence of a specific component without reducing the value of the product.

A weight inspection system according to a twelfth aspect of the present invention includes the weight inspection apparatus according to any one of the first through eleventh aspects of the present invention, and a weight measuring device arranged on the upstream side of the weight inspection apparatus and configured to measure the actual weight of the inspection target object.

Accordingly, when the deviation amount between the actual weight and the estimated weight is larger than a predetermined value, for example, this situation can be detected as an occurrence of a defect in either the weight measuring device or the weight inspection apparatus, a correction value to calculate the estimated weight by the weight inspection apparatus can be adjusted, and/or this situation can be used for calculation of the weight of each of a plurality of components having different specific gravities. As a result, it is possible to provide the weight inspection system capable of improving the precision of the calculated weight of the inspection target object.

BRIEF DESCRIPTION OF THE DRAWINGS

FIG. 2 is a perspective view showing a configuration of the X-ray inspection apparatus included in the X-ray inspection system in FIG. 1.

FIG. 3 is a simplified schematic view showing internal components inside a shield box of the X-ray inspection apparatus of FIG. 1.

FIG. 6 is a function block diagram generated as a CPU of the control computer in FIG. 5 loads an X-ray inspection program.

FIG. 7 is a graph that indicates a relationship between the brightness per unit area included in an X-ray transmission image and the thickness of a material in the area.

FIG. 11 is a graph for a value R which is used when calculating the weight of each component by the X-ray inspection apparatus in FIG. 2.

FIG. 12 is a perspective view showing a configuration of a weight inspection apparatus according to another embodiment of the present invention.

BEST MODE FOR CARRYING OUT THE INVENTION

An X-ray inspection system (weight inspection system) including an X-ray inspection apparatus (weight inspection apparatus) 10 according to an embodiment of the present invention is described below with reference to FIGS. 1 to 11.

Configuration of X-Ray Inspection System 1

Figure 1:
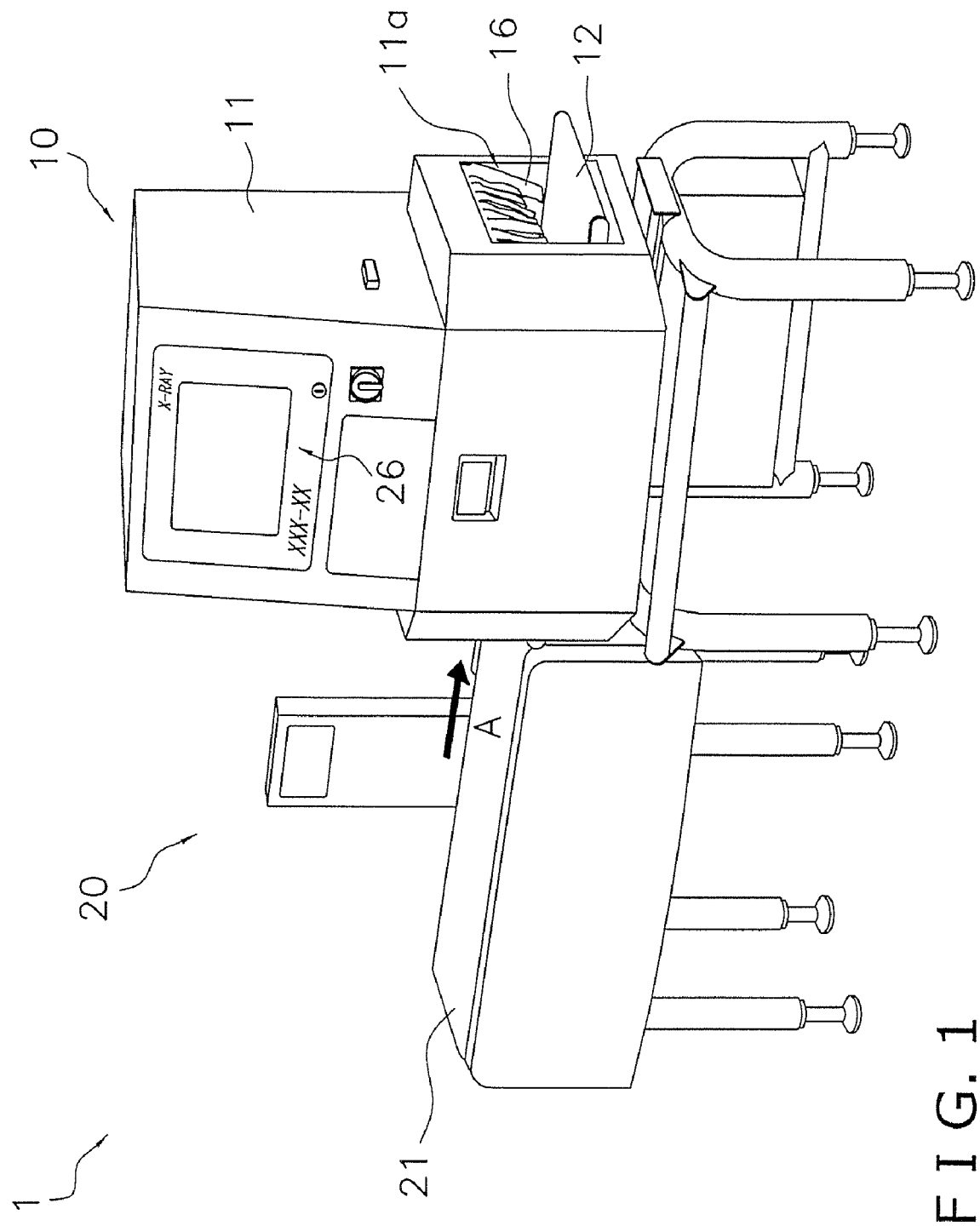
FIG. 1 is a perspective view showing an overall configuration of an X-ray inspection system including an X-ray inspection apparatus according to an embodiment of the present invention.

As shown in FIG. 1, an X-ray inspection system 1 in this embodiment includes the X-ray inspection apparatus 10 and a weight checker (weight measuring device) 20.

The X-ray inspection apparatus 10 irradiates a product (inspection target object) G being conveyed from the weight checker 20 arranged on the upstream side with X-rays, and creates an X-ray image by detecting the amount of transmitted X-rays. Then, the X-ray inspection apparatus 10 calculates the estimated weight of the product G based on the created X-ray image. Further, the X-ray inspection apparatus 10 obtains the actual weight of the product G from the weight checker 20 arranged on the upstream side, and based on the deviation amount between the actual weight and the above described estimated weight, calculates the weight and content percentage of a plurality of components having different specific gravities contained in the product G, and/or detects the presence of a defect in the measured weight (estimated value) by the weight checker 20 or the X-ray inspection apparatus 10. Note that, in this embodiment, calculation by the X-ray inspection apparatus 10 for the weight (content percentage) of each of the components having different specific gravities contained in the product G is described in a later section.

Figure 5:
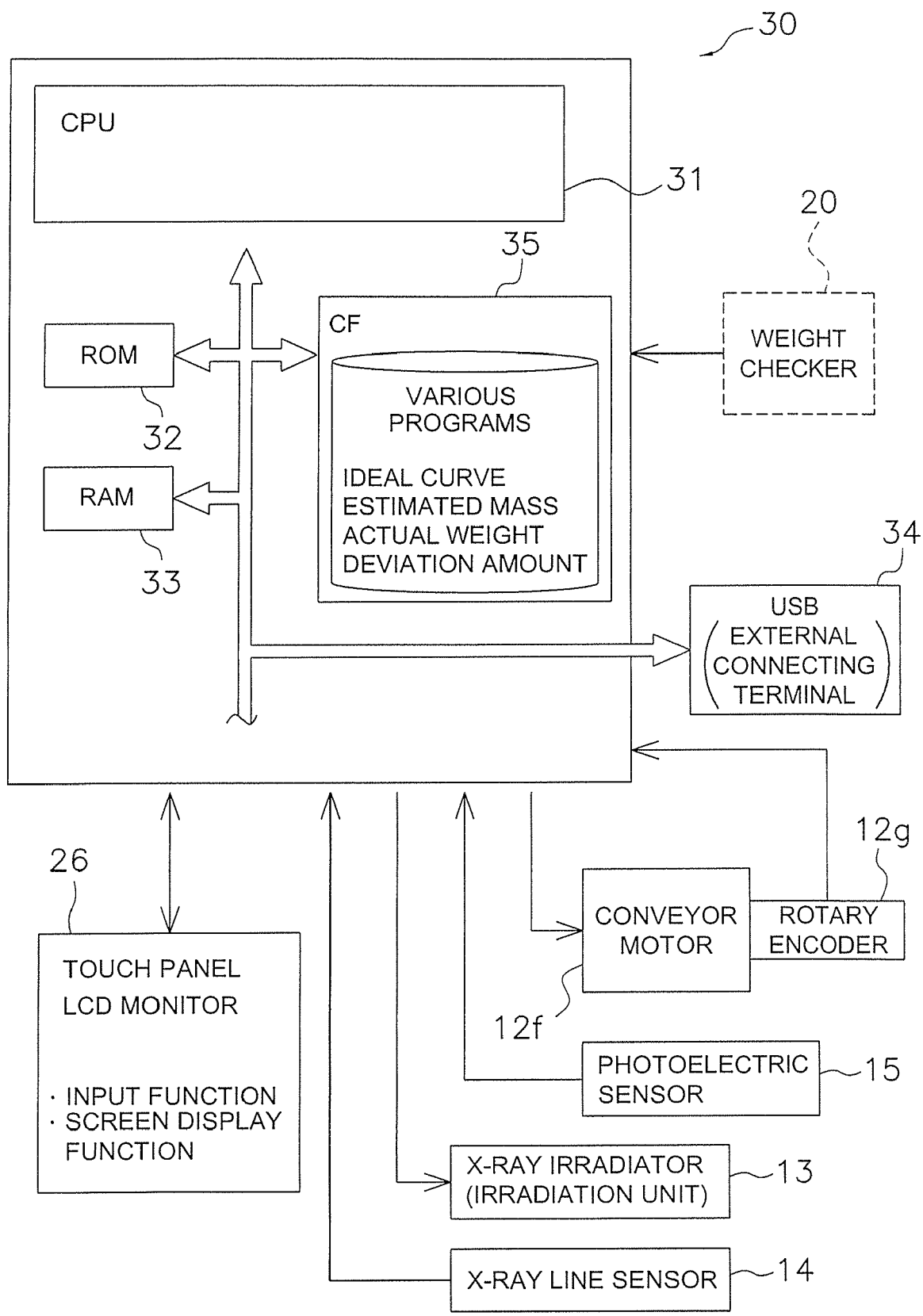
FIG. 5 is a control block diagram showing a configuration of a control computer included in the X-ray inspection apparatus in FIG. 1.

The weight checker 20 is arranged on the upstream side of the X-ray inspection apparatus 10, and configured to measure the gross weight of the product G conveyed from upstream while conveying the same by a conveyor 21 and to transmit the measured value to the X-ray inspection apparatus 10 arranged on the immediate downstream side (see FIG. 5).

Entire Configuration of X-Ray Inspection Apparatus 10

As shown in FIG. 1, in the production line of product such as food products and the like, the X-ray inspection apparatus 10 in this embodiment irradiates the product G being continuously conveyed with X-rays, estimates the mass of the product based on an X-ray image created by detecting the amount of X-rays transmitted through the product, and inspects whether or not the estimated mass is within a predetermined range. Then, based on the estimated weight which is calculated here and the actual weight, the weight of each of the plurality of components having different specific gravities contained in the product G is estimated. Note that an example is described below in which the meat product containing a meat portion and a fat portion each having a different specific gravity is used as the product G.

As shown in FIG. 2, the X-ray inspection apparatus 10 mainly comprises a shield box 11, a conveyor 12, a shielding curtain 16, and a monitor 26 with a touch panel function. Further, as shown in FIG. 3, the inside of the X-ray inspection apparatus 10 is provided with an X-ray irradiator (irradiation unit) 13, an X-ray line sensor (X-ray detection unit) 14, and a control computer (sample image obtaining unit, table generating unit, table adjustment unit, estimated mass calculation unit, weight obtaining unit, deviation amount calculation unit, and component weight calculation unit) 30 (see FIG. 5).

Shield Box 11

As shown in FIG. 2, the shield box 11 has an opening 11a on an entrance side and an exit side for the product G, and through which products are carried into and out of the shield box 11. As shown in FIG. 3, inside this shield box 11 are housed the conveyor 12, the X-ray irradiator 13, the X-ray line sensor 14, the control computer 30 (see FIG. 5) and the like.

In addition, as shown in FIG. 2, the opening 11a is covered with the shielding curtain 16 in order to prevent X-rays from leaking out of the shield box 11. The shielding curtain 16 is partially made of rubber that contains lead, and is pushed aside by a product when the product is carried in and out of the shield box 11.

In addition, on the upper part of the front surface of the shield box 11 are disposed such as a key hole and a power switch adjacent to the monitor 26.

Conveyor 12

The conveyor 12 serves to convey products into and out of the shield box 11, and is driven by a conveyor motor 12f included in the control block shown in FIG. 5. The conveying speed of the conveyor 12 is precisely controlled by controlling an inverter for the conveyor motor 12f by the control computer 30 so as to match the conveying speed with the setting speed input by an operator.

In addition, as show in FIG. 3, the conveyor 12 includes a conveyor belt 12a and a conveyor frame 12b, which are removably attached to the shield box 11. In this way, when conducting inspection of a food product and the like, the conveyor 12 can be removed and washed frequently to keep the inside of the shield box 11 clean.

The conveyor belt 12a is an endless belt, and the inside of the belt is supported by the conveyor frame 12b. The conveyor belt 12a rotates by receiving a driving force of the conveyor motor 12f, and consequently the conveyor belt 12a conveys an object placed on the belt in a predetermined direction.

The conveyor frame 12b supports the endless conveyor belt 12a from the inside thereof. Also, as shown in FIG. 3, the conveyor frame 12b has an opening 12c, which opens lengthwise in a direction perpendicular to the conveyance direction, at a position opposing the inner side of the conveyor belt 12a. The opening 12c is formed on a line, which connects the X-ray irradiator 13 and the X-ray line sensor 14, on the conveyor frame 12b. In other words, the opening 12c is formed at an area where X-rays are irradiated toward by the X-ray irradiator 13 on the conveyor frame 12b, in order to prevent the X-rays transmitted through the product G from being blocked by the conveyor frame 12b.

X-Ray Irradiator 13

As shown in FIG. 3, the X-ray irradiator 13 is disposed above the conveyor 12 and performs fan-shaped X-ray irradiation through the opening 12c formed in the conveyor frame 12b toward the X-ray line sensor 14 disposed below the conveyor 12 (see the shaded area in FIG. 3).

X-Ray Line Sensor 14

Figure 4:
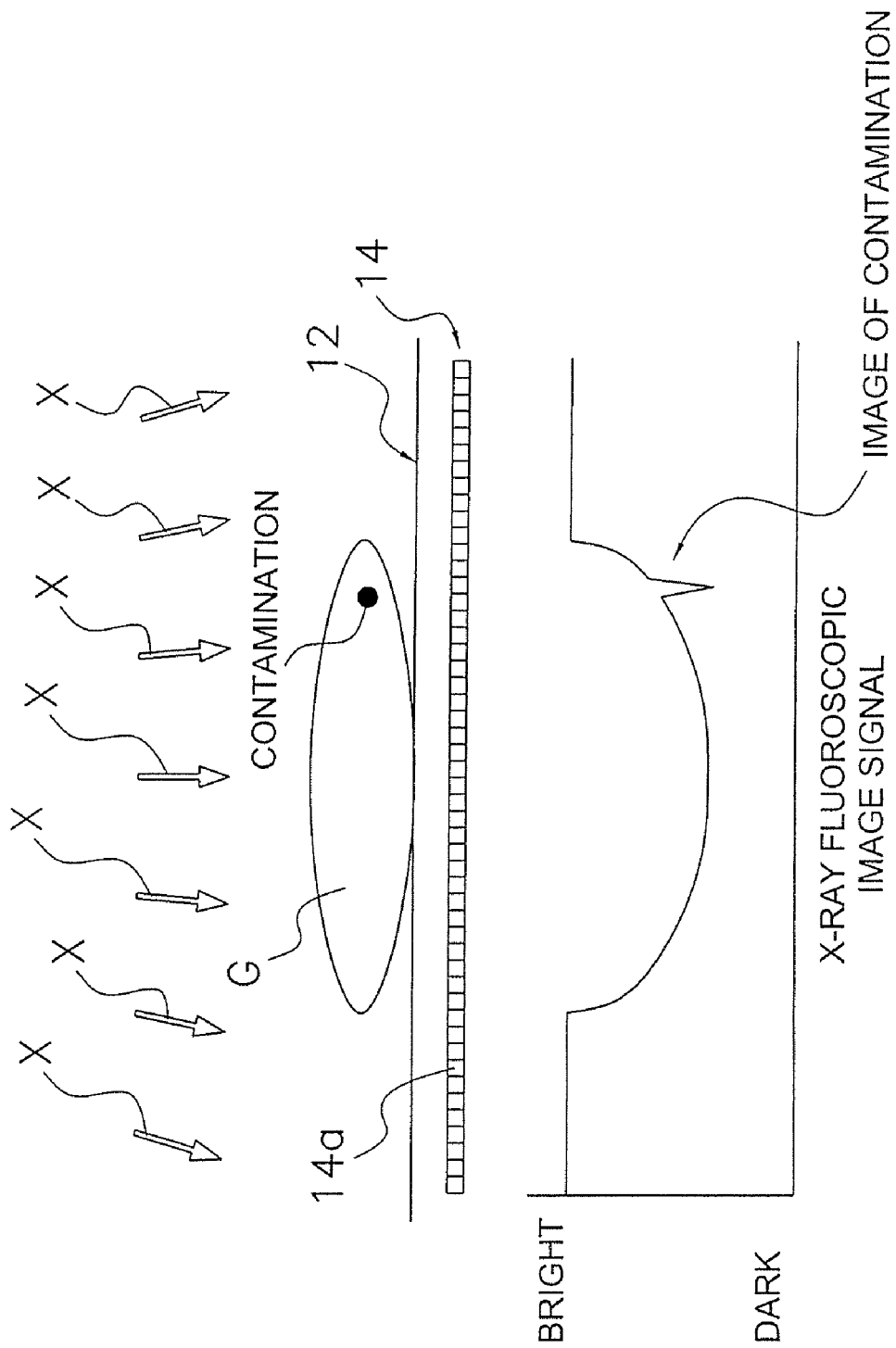
FIG. 4 is a schematic view showing the principle of inspection of contamination performed by the X-ray inspection apparatus in FIG. 1.

The X-ray line sensor 14 is disposed below the conveyor 12 (the opening 12c), and detects X-rays transmitted through the product G and the conveyor belt 12a. As shown in FIG. 3 and FIG. 4, this X-ray line sensor 14 comprises a plurality of pixels 14a arranged horizontally in a straight line in a direction perpendicular to the transport direction of the conveyor 12.

Note that FIG. 4 depicts a state of X-ray irradiation in the X-ray inspection apparatus 10 and a graph that indicates the amount of X-rays detected at that time at each pixel 14a constituting the X-ray line sensor 14.

Monitor 26

The monitor 26 is a full-dot liquid crystal display. In addition, the monitor 26 is equipped with a touch panel function and displays a screen that requests parameter input and the like regarding initial settings, judgment after mass estimation, and the like.

In addition, the monitor 26 displays an X-ray transmission image of the product G, which is created based on a result of detection by the X-ray line sensor 14 and which subsequently has undergone image processing. Accordingly, it is possible to have the user visually recognize a state inside the product G, for example, a state in which powder is concentrated in one portion and the like.

Control Computer 30

The control computer 30 executes, in a CPU 31, an image processing routine, an inspection determination processing routine, and the like, which are included in a control program. In addition, the control computer 30 saves and accumulates, in a storage unit such as a CF (COMPACT FLASH: registered trademark) 35, X-ray images and inspection results of defective products, correction data of X-ray images, and the like. Further, control computer 30 receives the actual weight of the product G from the weight checker 20 arranged on the upstream side in the production line, thereby functioning as an actual weight obtaining unit.

As a specific structure, as shown in FIG. 5, the control computer 30 is mounted with the CPU 31, and is also mounted with a ROM 32, a RAM 33, and the CF 35 as main storage units, which are controlled by the CPU 31.

The CF 35 stores various programs to control each unit, various information regarding X-ray transmission images which serve as the basis of mass estimation, ideal curve, estimated mass, actual weight of the product G, deviation amount between the actual weight and the estimated mass, and the like.

Further, the control computer 30 is equipped with a display control circuit that controls the display of data on the monitor 26, a key input circuit that fetches key input data from the touch panel of the monitor 26, an I/O port for controlling data printing by a printer (not shown), a USB 34 and the like as an external connection terminal.

The CPU 31, the ROM 32, the RAM 33, the CF 35, and the like are connected each other through a bus line, such as an address bus or a data bus.

Further, the control computer 30 is connected to the conveyor motor 12f, a rotary encoder 12g, the X-ray irradiator 13, the X-ray line sensor 14, and a photoelectric sensor 15 and so on.

The control computer 30 receives the conveying speed of the conveyor 12 detected by the rotary encoder 12g attached to the conveyor motor 12f.

In addition, the control computer 30 receives signals from the photoelectric sensor 15 as a synchronization sensor, which is configured from a light projecting device and its corresponding light receiving device disposed so as to sandwich the conveyor unit, and detects the timing at which the product G, which is the inspection target object, reaches the position of the X-ray line sensor 14.

Function Block Created by Control Computer 30

In this embodiment, the CPU 31 of the control computer 30 loads an X-ray inspection program stored in the CF 35, and creates function blocks as shown in FIG. 6.

Specifically, as shown in FIG. 6, a sample image obtaining unit 41, a table forming unit (ideal curve generating unit) 42, a table adjustment unit (curve adjustment unit) 43, an estimated mass calculation unit 44, a deviation amount calculation unit 45, and a component weight calculation unit 46 are created as function blocks in the control computer 30.

The sample image obtaining unit 41 obtains X-ray transmission images of the ten products G whose mass is known in advance (hereinafter, the mass of each of the ten products G is referred to as "actual mass").

For a brightness "a" per unit area (1 pixel) obtained by the sample image obtaining unit 41, the table forming unit 42 generates a table (ideal curve) m(a) based on the following formula (2) for calculating an estimated mass m of the area.

$$m = ct = -c/\mu \times \ln(I/I_0) = -\alpha \ln(I/I_0) \quad (2)$$

In the formula (2) above, a value m represents the estimated mass, a value c represents a coefficient for converting the thickness of a material to the mass, a value t represents a thickness of the material, a value I represents a brightness based on the detected X-ray when there is no material, a value $I_0$ represents a brightness based on the detected X-ray transmitted through material, a value μ represents a line absorption coefficient.

The table adjustment unit 43 compares the actual mass of each of the ten products G input via the monitor 26 to the total estimated mass obtained by adding up the estimated mass at each gradation level determined by the above table (ideal curve), and adjusts the table such that each total estimated mass approximates the actual mass.

The estimated mass calculation unit 44 obtains the estimated mass per unit area in a manner corresponding to the brightness per unit area (1 pixel) based on the table (ideal curve) adjusted by the table adjustment unit 43, and calculates the estimated mass of each the product G by adding up these masses.

Note that a method for estimating the mass by each of these function blocks 41 to 44 is described later in detail.

The deviation amount calculation unit 45 calculates the deviation amount between the actual weight of the product G measured by the above described weight checker 20 and the estimated weight calculated by the above described estimated mass calculation unit 44.

The component weight calculation unit 46 calculates the weight of a meat portion (component B) and the weight of a fat portion (component A) contained in the product G which is a meat product, following the relational expression (1) below, based on the actual weight of the product G measured by the above described weight checker 20 and the estimated weight calculated by the above described estimated mass calculation unit 44.

$$r = (1 - W2/W1) \times 100/(1-R) \quad (1)$$

In the formula (1) above, a value r represents a content percentage of the component A, a value R represents a weight ratio between when the content percentage of the component A is 100% and when the content percentage of the component A is 0%, a value W1 represents the actual weight, and a value W2 represents the estimated weight.

Note that R is calculated in advance for each product.

Control Flow of Mass Estimation by Control Computer 30

Here, first, a calculation flow for the estimated mass of the product G by the X-ray inspection apparatus 10 is described as follows.

In general, in the relationship between the thickness of a material and the brightness of the corresponding portion (brightness when there is no material is defined as the normalized brightness of 1.0) in the X-ray transmission image obtained, it is known that errors are generated as shown in FIG. 7 between a graph ($I/I_0 = ^{-\mu t}$) represented by an exponential function as in the above described formula (2) and a graph indicating the actual mass. In particular, in the graph that indicates the actual mass, the brightness is drastically reduced in an area where the thickness "t" is relatively small. This occurs because an X-ray whose energy is relatively small is preferentially absorbed and an X-ray becomes harder each time passing through a material. Further, as described above, the brightness of the X-ray transmission image includes, in addition to factors such as X-ray energy distribution and the thickness of a material, uncertain factors such as use of a specific filter, energy characteristics of the X-ray inspection apparatus, factors relating to image preprocessing such as gamma correction, and the like.

Figure 8:
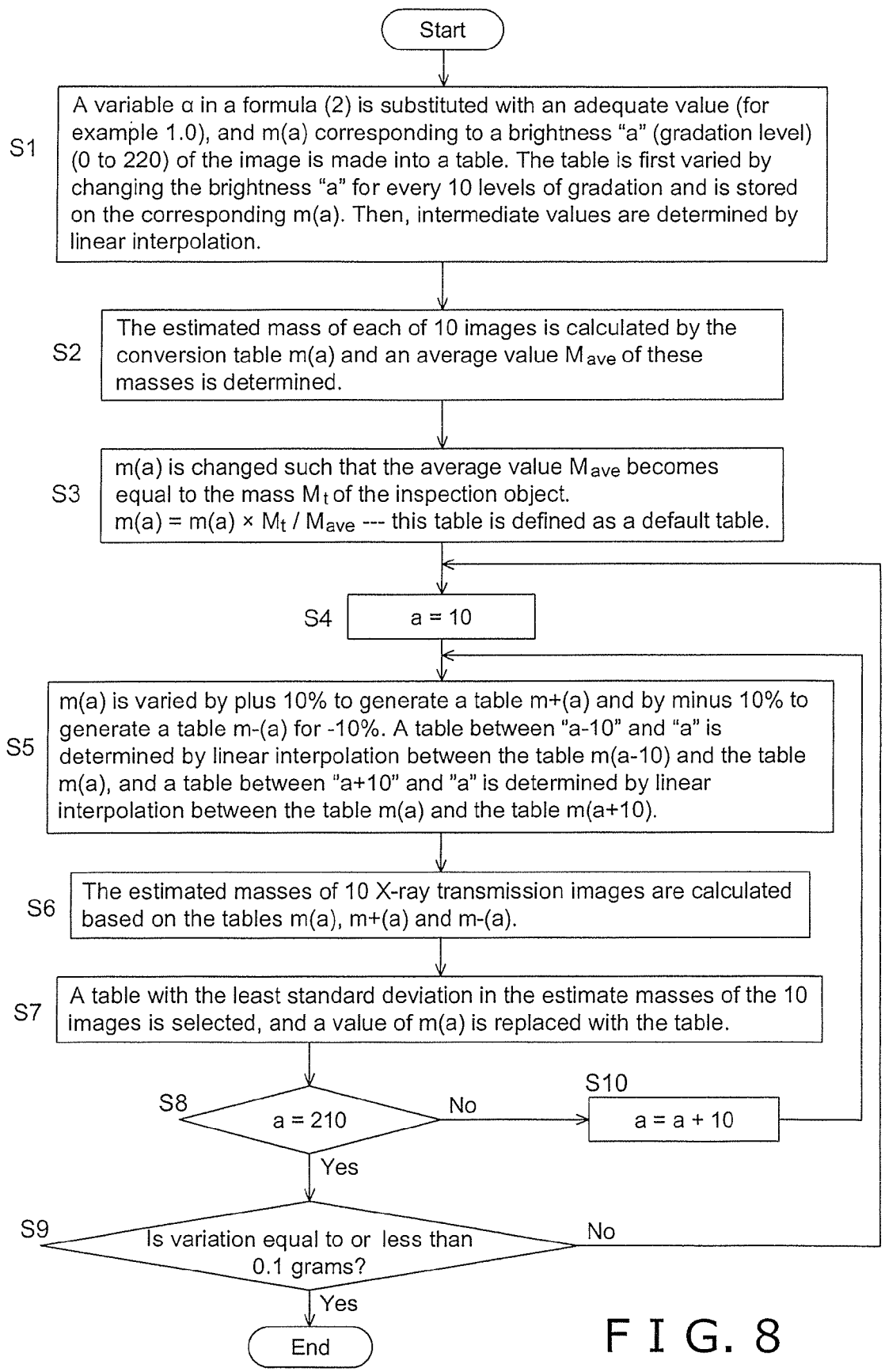
FIG. 8 is a flowchart showing a flow of a mass estimation control based on the X-ray inspection program by the X-ray inspection apparatus in FIG. 1.

With the X-ray inspection apparatus 10 in this embodiment, estimation of the mass is performed following the flowchart shown in FIG. 8, in order to estimate the mass with high precision by eliminating an uneven concentration of each component of the product G and the influence of various uncertain factors.

Figure 9:
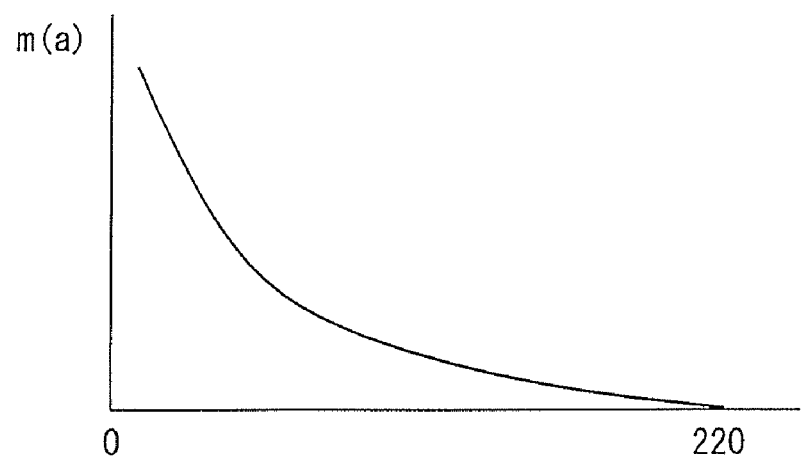
FIG. 9($a$) is a graph showing a table m(a) before a coefficient α is optimized, and FIG. 9($b$) is a graph showing a table m(a) after the coefficient α is optimized.
Figure 9:
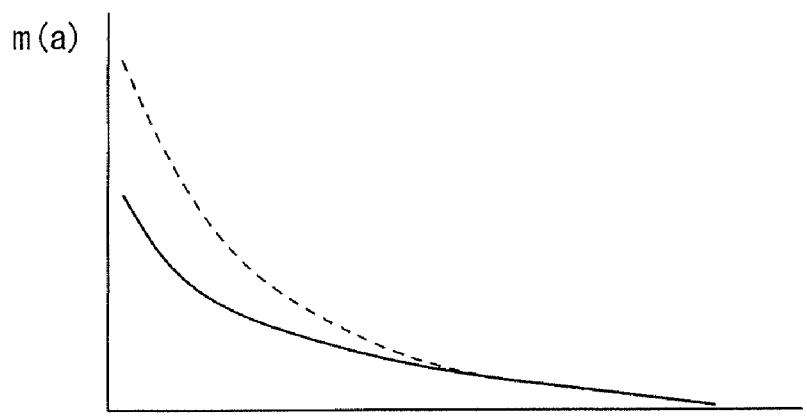

In other words, in step S1, for example, α in the above described formula (2) is substituted with a value of 1.0, and the estimated mass m(a) corresponding to the image brightness (gradation level) "a" (0 to 220) is made into a table. The table generated based on the formula (2) is first varied by changing the brightness "a" for every ten levels of gradation and is stored on a table corresponding to m(a). Then, intermediate values are determined by linear interpolation. Accordingly, the table forming unit 42 of the control computer 30 generates a table (ideal curve) as shown in FIG. 9(*a*), which indicates a relationship between the brightness and the estimated mass m(a). Note that, in view of that it takes too much time to obtain all the estimated mass of the unit area at each brightness level following the formula (2), here, the estimated mass is obtained for every ten levels of gradation by the formula (2) and the intermediate values are determined by linear interpolation.

In step S2, the sample image obtaining unit 41 irradiates, with X-rays, the ten products G each of whose mass is known to be 200 grams in advance and thereby obtains ten X-ray transmission images. Then, the estimated masses of the ten X-ray transmission images obtained are calculated by the conversion table m(a), and an average value Mave of these masses is determined. Note that, in order to obtain a broader range of brightness data, it is preferable that ten sample images include an image of a product in which the powder is concentrated in one portion in the bag, an image of a product in which the powder is evenly dispersed, and the like.

In step S3, m(a) is changed following the relational expression (3) below such that the average value Mave determined in step S2 becomes equal to the mass Mt of the inspected object, and a table after the change as shown by a solid line in FIG. 9(*b*) is defined as a default table (ideal curve). Note that in FIG. 9(*b*), the dotted line indicates a table before the change, and the solid line indicates a default table (ideal curve) after the change.

$$m(a)=m(a) \times Mt/Mave \qquad (3)$$

In step S4, a value 10 is substituted for the brightness "a" in the ideal curve (e.g., FIG. 9(*b*)) in order to determine the estimated mass m(a). Here, the brightness "a" is substituted by a number starting with a value 10, and then with values 20, 30, . . . when steps S4-S8 are repeated subsequently. This is because the estimated mass would become infinite if the brightness "a" is substituted by a value 0. Accordingly, the estimated mass may be determined by starting out by substituting a value 1 for the brightness "a" followed by values 11, 21, 31, . . . .

In step S5, in order to examine changes caused by gradually shifting the table m(a) up and down, the table m(a) is varied by plus minus 10% to generate a new table m+(a) and a new table m−(a). At this time, a table between "a−10" and "a" is determined by linear interpolation between the table m(a−10) and the table m(a), and a table between "a+10" and "a" is determined by linear interpolation between the table m(a) and the table m(a+10), and thereby the table m+(a) and the table m−(a) are generated.

In step S6, the estimated mass of each of the ten X-ray transmission images is calculated based on the two new tables generated in step S5, i.e., the table m+(a) and the table m−(a), and the original table m(a).

In step S7, a table with the least standard deviation (least variation) based on the estimated masses corresponding to each of the ten X-ray transmission images, which are calculated by using the three tables m(a), m+(a), and m−(a) in step S6, is selected, and the table m(a) is replaced with this table.

For example, when the table m+(a) has lower standard deviation than the table m(a) in a certain brightness (gradation level) "a", the table m(a) is replaced with the table m+(a) for a portion corresponding to the brightness "a." On the other hand, when the table m(a) has lower standard deviation than the table m+(a), the table m(a) will not be replaced but maintained as is for a portion corresponding to the brightness "a".

Figure 10:
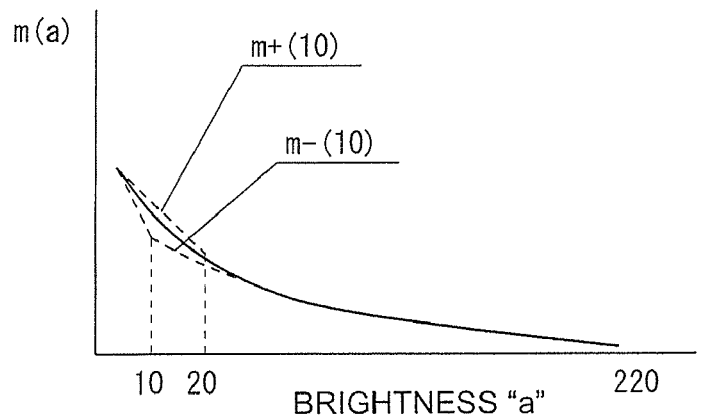
FIGS. 10($a$) to ($c$) are graphs to represent a process in which a conversion table m(a) is optimized.
Figure 10:
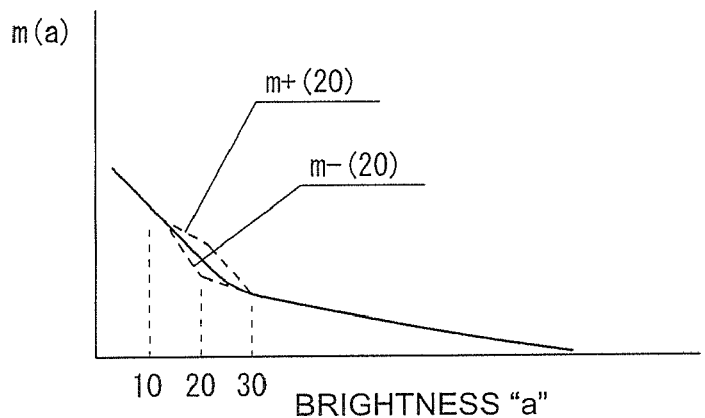
Figure 10:
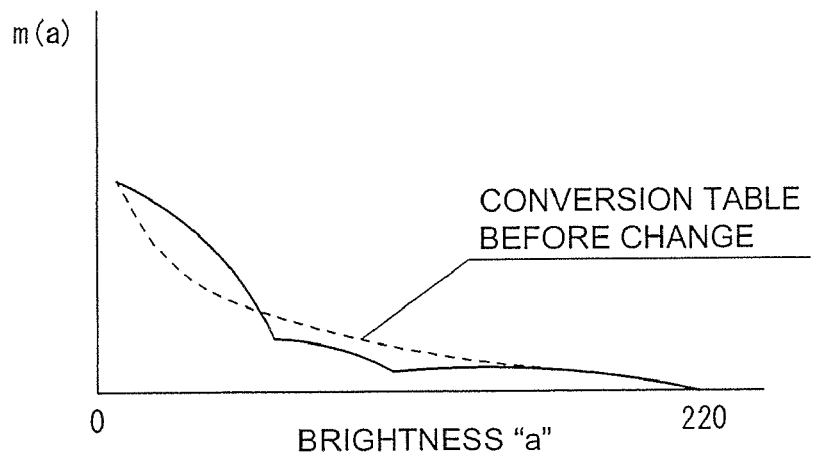

Specifically, as shown in FIG. 10(*a*), in a portion where the brightness (a) is equal to 10, the standard deviation is compared among the table m(10) shown by a solid line, the table m+(10) shown by a dotted line above, and the table m−(10) shown by a dotted line below, and the table m+(10) with the least standard deviation is selected. Consequently, as shown in FIG. 10(*b*), in a portion where the brightness (a) is equal to 10, the table m (10) is replaced with the table m+(10).

In step S8, whether or not the brightness "a" is 210 is determined, and when the answer is "no," the process proceeds to step S10, and the replacement process of the table m(a) in the above described step S7 is repeated by increasing the brightness "a" by 10 until the brightness "a" is 210.

In other words, replacement of the table is repeated in the same way for cases where the brightness "a" is equal to 20, 30, 40, . . . , in order to generate the table shown by a solid line in FIG. 10(*c*).

Note that the process in step S7 corresponds to the adjustment process of the table, i.e., the ideal curve performed by the table adjustment unit 43.

In step S9, the masses of the ten X-ray transmission images are determined in accordance with the post-adjusted table m(a) obtained by the replacement process, and whether or not the value of variation in the mass is equal to or less than 0.1 grams. Here, when the value is equal to or greater than 0.1 grams, the process returns to step S4 and the above described process is repeated until the value of variation become equal to or less than 0.1 grams.

Through the above described process, the X-ray inspection apparatus 10 of the present embodiment generates the conversion table m(a) (see FIG. 10(*c*)) for estimating the mass of the product G from the X-ray transmission image of the product G. Accordingly, by estimating the mass of the product G to be inspected by using the optimized, post-adjusted conversion table m(a) as shown in FIG. 10(*c*), it is possible to achieve estimation of the mass with high precision, compared to a conventional mass estimation method that depends on the formula.

Control Flow of Calculation of Weight of Each Component by Control Computer 30

In this embodiment, besides the above described calculation of the estimated weight, the weight of a meat portion and the weight of a fat portion each having a different specific gravity and being contained in the product G, are calculated using the actual weight measured by the weight checker 20.

Specifically, provided that the actual weight of the product G which is a meat product is 200 grams and the estimated weight calculated by the above described X-ray inspection apparatus 10 is 192 grams, the content percentage of each component (weight of the fat portion) is calculated based on the following relational expression (1), which was described above.

$$r=(1-W2/W1) \times 100/(1-R) \qquad (1)$$

(r: content percentage of a fat portion, R: a weight ratio between when the content percentage of the fat portion is 100% and when the content percentage of the fat portion is 0% (here, R=0.9), actual weight W1, estimated weight W2).

Here, in order to have the X-ray inspection apparatus 10 learn about the meat product with a fat percentage of 0% in advance, the conversion function of the X-ray inspection apparatus 10 is set such that the smaller the fat portion is, the closer the actual weight measured by the weight checker 20 is to the estimated weight estimated by the X-ray inspection apparatus 10.

At the same time, by providing a ratio (R) of the weight when the fat portion accounts 100% to the weight when the fat portion accounts 0% in advance (see FIG. 11), it will be possible to calculated the content percentages and the weights of the meat portion and the fat portion having different specific gravities, using the above described relational expression (1).

When an actual weight of 200 grams, an estimated weight of 192 grams, an R=0.9 are substituted into the relational expression (1), the weight content percentage "r" of the fat portion will be as follows:

$$r = (1-192/200) \times 100/(1-0.9)$$
$$= 4/0.1$$
$$= 40.0(\%)$$

Therefore, the weight content percentage of the fat portion contained in the product G which is a meat product can be calculated to be 40.0% and the weight content percentage of the remaining meat portion can be calculated to be 60.0%.

As a result, because it is determined that the meat portion accounts for 60.0% and the fat portion accounts for 40.0% of the weight (200 grams) of the product G, the weight of the meat portion can be calculated to be 120 grams and the weight of the fat portion can be calculated to be 80 grams.

Characteristics of X-Ray Inspection Apparatus 10

(1) In the X-ray inspection apparatus 10 in this embodiment, the deviation amount calculation unit 45 calculates the degree of the discrepancy of the estimated weight from the actual weight, based on the above described actual weight of the product G which is externally obtained and the estimated weight of the product G calculated by each of the function blocks 41 to 44 formed in the control computer 30 as shown in FIG. 6.

Accordingly, compared to the calculation of the weight by a conventional X-ray inspection apparatus, it is possible to improve the measurement precision by calculating the estimated weight and the weight of each component using a result of comparison between the actual weight and the estimated weight for the degree of the discrepancy, instead of using the estimated weight, as is, which is calculated using the X-ray image and the like. In addition, by obtaining the actual weight and comparing it with the estimated weight, it is possible to easily detect a reduction in the precision of the estimated weight. Accordingly, for example, based on the degree of the deviation between the actual weight and the estimated weight, it is possible to take countermeasures such as adjusting a correction value which is used when calculating the estimated weight and the like.

(2) In the X-ray inspection apparatus 10 in this embodiment, the component weight calculation unit 46 calculates the weight of each of the components having different specific gravities which are contained in the product G, based on the above described actual weight of the product G externally obtained and the estimated weight of the product G calculated by each of the function blocks 41 to 44 formed in the control computer 30 as shown in FIG. 6.

Accordingly, when the product G is a meat product, the weight (content percentage) of the meat portion and the weight (content percentage) of the fat portion can be easily calculated with high precision. As a result, it is possible to improve the quality control of the product G by determining the amount of a bone portion of the meat with bone, judging the degree of the marbling of the meat, selecting a product with a fat portion whose content percentage is equal to or greater than a predetermined percentage, discarding unwanted products and the like. In addition, even when calculating the weights of a plurality of components having different specific gravities, a single unit of the X-ray line sensor 14 can be used. Thus, it is possible to simplify the configuration of the apparatus and reduce the cost, compared with a conventional X-ray inspection apparatus having a plurality of X-ray line sensors.

(3) In the X-ray inspection apparatus 10 in this embodiment, as shown in FIGS. 1 and 5, the actual weight of the product G is obtained from the weight checker 20 arranged on the upstream side in the production line.

Accordingly, it is possible to perform the process from the obtainment of the actual weight to the calculation of the estimated weight and to the calculation of the weight of each of the components having different specific gravities which are contained in the product G while the product G is being conveying along the production line.

(4) In the X-ray inspection apparatus 10 in this embodiment, the component weight calculation unit 46 included in the function blocks shown in FIG. 6 calculates the weight of each of the components having different specific gravities which are contained in the product G based on the above described relational expression (1).

Accordingly, it is possible to easily calculate the weight of each component by combining the estimated weight calculated by the X-ray inspection apparatus 10 and the actual weight obtained by the weight checker 20 and the like.

(5) In the X-ray inspection apparatus 10 in this embodiment, the estimated weight of the product G is calculated based on such as the brightness of each pixel in the X-ray image by the each of the units 41 to 44 included in the function blocks shown in FIG. 6.

Accordingly, because the estimated weight can be calculated using the X-ray image created by the X-ray inspection apparatus 10, it is possible to easily obtain the actual weight and the estimated weight.

(6) In the X-ray inspection system 1 in this embodiment, as shown in FIGS. 1 and 5, the actual weight of the product G is obtained from the weight checker 20 arranged on the upstream side which constitutes the production line, and calculates the weight of each of the components having different specific gravities by the X-ray inspection apparatus 10, based on the estimated weight calculated by the X-ray inspection apparatus 10 and the actual weight.

Accordingly, it is possible to configure the X-ray inspection system 1 capable of performing the process from the obtainment of the actual weight to the calculation of the estimated weight and to the calculation of the weight of each of the components having different specific gravities, which are contained in the product G, while conveying the product G along the production line.

Alternative Embodiments

While a preferred embodiment has been described in connection with the present invention, the scope of the present invention is not limited to the above embodiment, and various changes and modifications may be made without departing from the scope of the present invention.

(A) The above embodiment is described taking an example in which the present invention is applied to the X-ray inspection apparatus 10 that detects the amount of transmitted X-rays used to irradiate the product (inspection target object) G and calculates the estimated weight of the product G. However, the present invention is not limited thereto.

For example, the present invention can be applied to a weight inspection apparatus that inspects the weight using different energy waves such as terahertz waves, millimeter waves, submillimeter waves, infrared rays and the like, instead of X-rays, to irradiate the inspection target object.

Here, when the weight is inspected by irradiating the inspection target object with terahertz waves, a weight inspection apparatus 110 as shown in FIG. 12 can be used. Specifically, the weight inspection apparatus 110 is an apparatus that measures the weight of the product G and also calculates the content percentage and the weight of each of a plurality of components contained in the product G, and mainly includes an inspection unit (spectroscope unit) 111, a weighing unit 112, a display unit 115, and a control unit.

The inspection unit 111 is arranged above a weighing table 112a on which the product G is placed in a state of being supported by a case 111a, and configured to irradiate the product G with terahertz waves which are a type of electromagnetic waves and detect the reflected waves to obtain the absorption spectrum having a plurality of wavelength components. In addition, the inspection unit 111 houses a terahertz wave irradiation unit 113 and a terahertz wave detection unit 114. The terahertz wave irradiation unit 113 irradiates the product G placed on the weighing table 112a with terahertz waves from above. The reflected terahertz waves used to irradiate the product G by the wave irradiation unit 113 is detected by the terahertz wave detection unit 114 to obtain the absorption spectrum having a plurality of wavelength components, and the terahertz wave detection unit 114 sends a result of detection to the control unit (not shown).

The weighing unit 112 is a weighing device mounted with a load cell (not shown) therein, and configured to measure the weight of the product G placed on the weighing table 112a. In addition, the weighing unit 112 sends a result of measurement of each product G to the control unit.

Accordingly, the control unit can determine the estimated weight, content percentage and the like of each component through obtainment of the absorption spectrum by detecting the terahertz waves reflected from the product G and comparison between the above described absorption spectrum and the absorption spectrum of each component contained in the inspection target object.

(B) The above embodiment is described taking an example in which the weight of each of the components (the meat portion and the fat portion) having different specific gravities which are contained in the product G is calculated based on the actual weight measured by the weight checker 20 and the estimated weight calculated by the X-ray inspection apparatus (weight inspection apparatus) 10. However, the present invention is not limited thereto.

For example, the present invention may have a configuration which, for example, determines that there is an error in the measurement of the actual weight by the weight checker when, for example, the difference between the actual weight measured by the weight checker and the estimated weight calculated by the weight inspection apparatus is calculated and when this difference is equal to or greater than a predetermined value. Alternatively, the present invention may have a configuration which corrects the estimated weight by the weight inspection apparatus correspondingly to the degree of the difference when the difference between the above described actual weight and the estimated weight is equal to or greater than a predetermined amount. Note that, in such a case, the above described control computer 30 may be caused to function as a judging unit that determines whether or not there is an error in the calculation of the estimated weight.

Also in these cases, it is possible to obtain the same effect as described above, i.e., the precision of the measured or estimated weight can be improved.

(C) The above embodiment is described taking an example in which a result of measurement by the weight checker 20 arranged on the upstream side is obtained in order to calculate the weight of each component contained in the product G as the inspection target object. However, the present invention is not limited thereto.

For example, it is possible to determine the weight and the content percentage of each component by providing a weighing unit that measures the actual weight of the inspection target object in the weight inspection apparatus and using the actual weight measured there.

In addition, it is possible to obtain data of the inspection target object that is already measured via a medium or the like and to use the data as the actual weight.

(D) The above embodiment is described taking an example in which the X-ray line sensor 14 is used as a detection unit that detects X-rays (energy waves) used to irradiate the product G. However, the present invention is not limited thereto.

For example, it is not limited to the X-ray line sensor that serves as a detection unit for detecting energy waves, but it is possible to use a camera or the like that captures reflected waves.

(E) The above embodiment is described taking an example in which the method that uses the X-ray image is employed as the means to determine the estimated weight of the product (inspection target object) G. However, the present invention is not limited thereto.

For example, it is possible to calculate the estimated weight based on the amount of X-rays in each pixel detected by a line sensor, which are transmitted through the inspection target object, without using an X-ray image.

(F) The above embodiment is described taking an example in which the precision of the calculation of the estimated weight is improved by correcting the ideal curve when determining the estimated weight of the product (inspection target object) G. However, the present invention is not limited thereto.

For example, it may be a weight inspection apparatus that calculates the estimated weight by a simpler method.

Also in this case, through the comparison between the actual weight and the estimated weight, it is possible to determine a reduction in the measurement precision in both of the actual weight and the estimated weight and to calculate the weight of each component contained in the inspection target object with high precision.

(G) The above embodiment is described taking a meat product containing a meat portion and a fat portion as an example of the product (inspection target object) G which serves as the target in which the weight of each component is calculated. However, the present invention is not limited thereto.

For example, even when the inspection target object is a different object, such as a packet of powdered soup and the like, which contains a plurality of components having different specific gravities, it is possible to calculate the mass of each component in the same manner as described above.

In addition, as for a plurality of components contained in the inspection target object, it is not limited to two kinds. It is possible to use a product containing three or more kinds of components having different specific gravities as the inspection target object.

The weight inspection apparatus of the present invention can achieve the effect of allowing a high precision calculation of the weight of each component of the inspection target object containing a plurality of components having different specific gravities, so that the weight inspection apparatus of the present invention is widely applicable as various types of inspection apparatuses that inspect food products, industrial products, and the like.

The invention claimed is:

1. A weight inspection apparatus comprising:
   a weight obtaining unit configured to obtain an actual weight of an inspection target object;
   an irradiation unit configured to irradiate the inspection target object with energy waves;
   a detection unit configured to detect the energy waves irradiated at the inspection target object;
   an estimated weight calculation unit configured to calculate an estimated weight of the inspection target object based on a result of detection by the detection unit;
   a deviation amount calculation unit configured to calculate a difference between the actual weight obtained by the weight obtaining unit and the estimated weight obtained by the estimated weight calculation unit; and
   a component weight calculation unit configured to calculate a weight of each of a plurality of components having different specific gravities contained in the inspection target object, based on the difference between the actual weight and the estimated weight.

2. The weight inspection apparatus according to claim 1, wherein
   the detection unit is configured to detect an amount of the energy waves transmitted through the inspection target object.

3. The weight inspection apparatus according to claim 1, wherein
   the detection unit is configured to detect an amount of the energy waves reflected from the inspection target object.

4. The weight inspection apparatus according to claim 1, wherein
   the weight obtaining unit is a weighing unit that measures the actual weight of the inspection target object.

5. The weight inspection apparatus according to claim 1, wherein
   the weight obtaining unit is configured to obtain the actual weight of the inspection target object from a weight measuring device arranged on an upstream side of the weight inspection apparatus.

6. The weight inspection apparatus according to claim 1, wherein
   the component weight calculation unit is configured to calculate a content percentage of a prescribed component among the components contained in the inspection target object, based on a following relational expression (1):

$$r=(1-W2/W1)\times100/(1-R) \qquad (1)$$

(where, r represents the content percentage of the prescribed component, R represents a weight ratio between when the content percentage of the prescribed component is 100% and when the content percentage of the prescribed component is 0%, W1 represents the actual weight of the inspection target object, and W2 represents the estimated weight of the inspection target object.

7. The weight inspection apparatus according to claim 1, wherein
   the irradiation unit is configured to irradiate X-rays as the energy waves.

8. The weight inspection apparatus according to claim 1, wherein
   the irradiation unit is configured to irradiate terahertz waves as the energy waves.

9. A weight inspection system comprising:
   the weight inspection apparatus according to claim 1; and
   a weight measuring device arranged on an upstream side of the weight inspection apparatus and configured to measure the actual weight of the inspection target object.

10. A weight inspection apparatus:
    a weight obtaining unit configured to obtain an actual weight of an inspection target object;
    an irradiation unit configured to irradiate the inspection target object with energy waves;
    a detection unit configured to detect the energy waves irradiated at the inspection target object;
    an estimated weight calculation unit configured to calculate an estimated weight of the inspection target object based on a result of detection by the detection unit;
    a deviation amount calculation unit configured to calculate a difference between the actual weight obtained by the weight obtaining unit and the estimated weight obtained by the estimated weight calculation unit; and
    an estimated weight adjusting unit configured to adjust a calculation result of the estimated weight by the estimated weight calculation unit, based on the difference between the actual weight and the estimated weight.

11. The weight inspection apparatus according to claim 6, wherein
    the detection unit is configured to detect an amount of the energy waves transmitted through the inspection target object.

12. The weight inspection apparatus according to claim 6, wherein
    the detection unit is configured to detect an amount of the energy waves reflected from the inspection target object.

13. The weight inspection apparatus according to claim 6, wherein
    the weight obtaining unit is a weighing unit that measures the actual weight of the inspection target object.

14. The weight inspection apparatus according to claim 6, wherein
    the weight obtaining unit is configured to obtain the actual weight of the inspection target object from a weight measuring device arranged on an upstream side of the weight inspection apparatus.

15. A weight inspection apparatus comprising:
    a weight obtaining unit configured to obtain an actual weight of an inspection target object;
    an irradiation unit configured to irradiate the inspection target object with energy waves;
    a detection unit configured to detect the energy waves irradiated at the inspection target object;
    an estimated weight calculation unit configured to calculate an estimated weight of the inspection target object using an image created based on an amount of the energy waves detected by the detection unit; and
    a deviation amount calculation unit configured to calculate a difference between the acutal weight obtained by the weight obtaining unit and the estimated weight obtained by the estimated weight calculation unit.

16. The weight inspection apparatus according to claim 15, wherein
the detection unit is configured to detect an amount of the energy waves transmitted through the inspection target object.

17. The weight inspection apparatus according to claim 15, wherein the detection unit is configured to detect an amount of the energy waves reflected from the inspection target object.

18. The weight inspection apparatus according to claim 15, wherein the weight obtaining unit is a weighing unit that measures the actual weight of the inspection target object.

19. The weight inspection apparatus according to claim 15, wherein the weight obtaining unit is configured to obtain the actual weight of the inspection target object from a weight measuring device arranged on an upstream side of the weight inspection apparatus.

* * * * *